United States Patent [19]

Tatsuta et al.

[11] Patent Number: 5,599,825
[45] Date of Patent: Feb. 4, 1997

[54] WATER-SOLUBLE METHINE COMPOUND AND PHARMACEUTICAL COMPOSITION FOR TREATMENT OF CANCER COMPRISING THE SAME

[75] Inventors: Noriaki Tatsuta; Akihiko Okegawa; Masayuki Kawakami, all of Minami-ashigara, Japan; Keizo Koya, Lexington, Mass.

[73] Assignee: Fuji Photo Film Co., Ltd., Kanagawa, Japan

[21] Appl. No.: 420,481

[22] Filed: Apr. 12, 1995

[30] Foreign Application Priority Data

Jul. 21, 1994 [JP] Japan .................. 6-169582

[51] Int. Cl.$^6$ .................. A61K 31/425; C07D 417/06
[52] U.S. Cl. .................. 514/366; 514/367; 514/369; 548/150; 548/152; 548/156; 548/159; 548/181; 548/182; 548/186; 548/184
[58] Field of Search .................. 514/366, 367, 514/369; 548/150, 152, 156, 159, 181, 182, 186, 184

[56] References Cited

U.S. PATENT DOCUMENTS 5,360,803  11/1994  Shishido et al. .................. 514/224.2

FOREIGN PATENT DOCUMENTS 3168634  7/1991  Japan .
4145431  5/1992  Japan .

OTHER PUBLICATIONS

CA 122: 187570p Preparation ... drugs. Ikegawa et al., p. 1056, 1995.
JP-A-3-168634, Photographic ... material, Hirabayashi, 1991.
JP-A-4-145431, Spectrally ... or the like, Okusa, 1992.

Primary Examiner—Joseph McKane
Attorney, Agent, or Firm—Sughrue, Mion, Zinn, Macpeak & Seas

[57] ABSTRACT

There are provided methine compounds having the following structure and their analogs, with a high solubility and are usefull as an active ingredient for pharmaceutical composition for treatment of cancer:

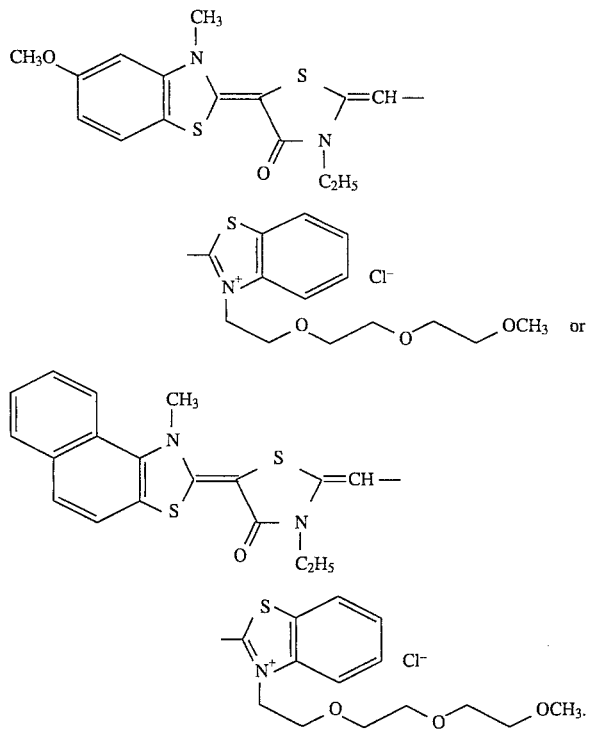

18 Claims, No Drawings

WATER-SOLUBLE METHINE COMPOUND AND PHARMACEUTICAL COMPOSITION FOR TREATMENT OF CANCER COMPRISING THE SAME

BACKGROUND OF THE INVENTION

The present invention relates to a methine compound useful as a photograhic material, medicine or the like, and to a pharmaceutical composition for treatment of cancer comprising the methine compound.

In the field of the photographic science, various methine compounds are described in, for example, U.S. Pat. Nos. 2,388,963, 2,454,629, 2,947,630, 3,979,213 and 3,796,733, French Patent Nos. 2,117,337 and 1,486,987, and West German Patent No. 2,140,323. These compounds are used as spectral sensitizing dyes. Among these, methine compounds which fall in rhodacyanine dyes usually have a low solubility, which causes a problem when they are incorporated into a photographic emulsion. For improving the solubility of these compounds, there is proposed a method wherein a hydroxyl group and methoxyethyl group are introduced into the molecular structure of each compound. Although such a method is disclosed in, for example, Japanese Patent Unexamined Published Application (hereinafter referred to as "J.P. KOKAI") Nos. Sho 63-228,145, 63-123,054 and 63-280,243, and Hei 3-168,634, 4-145,431 and 1-196,032, and European Patent No. 318,936, no satisfactory results have been obtained yet. Further, although the introduction of a sulfoalkyl group is also an ordinarily employed technique, this group seriously changes the charge of the compound, so that it is often that the essential properties of the compound cannot be maintained.

The medicinal effect of the methine compounds is expected in the medical and pharmaceutical fields, but the solubility is an important problem also in these fields and particularly in a medium having a high salt concentration such as blood in a living body, the precipitation or coagulation of such a compound is undesirable. For example, U.S. Pat. No. 5,360,803 and J.P. KOKAI Hei 6-80892 disclose compounds having a high solubility, but further improvement on the solubility is desired.

Thus, the solubility of the methine compounds is an important problem in both fields.

SUMMARY OF THE INVENTION

Therefore, an object of the present invention is to provide a methine compound which falls in rhodacyanine dyes and which has a high solubility.

Another object of the present invention is to provide a good pharmaceutical composition for treatment of cancer.

These and other objects of the present invention will be apparent from the following description and Examples.

The object of the present invention has been attained with a methine compound of the following formula (I):

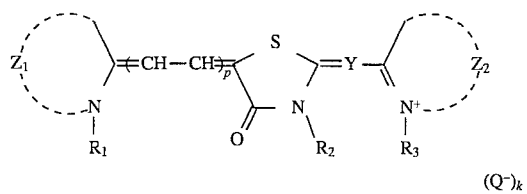

wherein Z, represents a non-metallic atomic group necessitated for forming a five-membered nitrogen-containing heterocyclic ring together with $-(R_1)-C-$, $Z_2$ represents a non-metallic atomic group necessitated for forming a five-membered nitrogen-containing heterocyclic ring together with $-N^+(R_3)=C-$, $R_1$, $R_2$ and $R_3$ each represent an alkyl group and at least one of $R_1$, $R_2$ and $R_3$ represents an alkyl group substituted with a polyethylene oxide group wherein one end of the polyalkylene oxide having a degree of polymerization of 2 to 6 is terminated with a hydrophobic group or substituted with a heterocyclic ring containing two or more oxygen atoms, Q represents an anion, k represents a numeral necessitated to control the charge in the molecule at zero, p represents 0 or 1, and Y represents a methine group or nitrogen atom.

There is also provided a pharmaceutical composition for treatment of cancer which comprises a therapeutically effective amount of the methine compound and a pharmaceutically acceptable diluent and/or carrier.

DESCRIPTION OF THE PREFERRED EMBODIMENTS

As the methine compounds represented by the above formula (I), those represented by the following formula (II) are preferred:

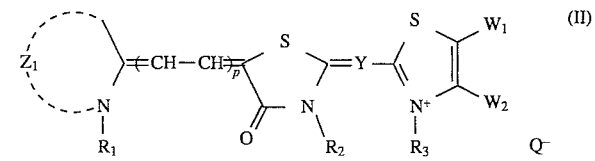

wherein $Z_1$ together with $-N(R_1)-C-$ represents a non-metallic atomic group necessitated for forming a thiazolidine ring, benzothiazoline ring, benzoxazoline ring, naphthothiazoline ring or naphthoxazoline ring, $W_1$ and $W_2$ each represent a hydrogen atom or they together form a non-metallic atomic group necessitated for forming a naphthalene condensed ring or benzene condensed ring, Q represents a halogen ion or organic acid anion, p represents 0 or 1, Y represents a methine group or nitrogen atom, $R_1$, $R_2$ and $R_3$ each represent an alkyl group and at least one of $R_1$, $R_2$ and $R_3$ has a substituent of the following formula III-a or III-b:

or

wherein $R_4$ represents an alkyl group having 2 or less carbon atoms, m represents 3 or 4 and n represents 2 or 3.

In particular, the heterocyclic rings formed by $Z_1$ and $-N(R_1)-C-$ together are preferably thiazolidine ring, benzothiazoline ring, naphthothiazoline ring and nahthoxazoline ring. More preferred are benzothiazoline ring and naphthothiazoline ring. Among them, benzothiazoline ring is the most preferred. The heterocyclic ring formed by $Z_1$ and $-N(R_1)-C-$ together may have a substituent. The substituent is preferably a halogen atom, alkyl group, alkoxy group, hydroxyl group or the like. The most preferred is methoxy group. The condensed ring formed by $W_1$ and $W_2$ may have a substituent, which is preferably a halogen atom, alkyl group, alkoxy group, hydroxyl group or the like. The alkyl groups represented by $R_1$, $R_2$ and $R_3$ are preferably those having 1 to 5 carbon atoms, more preferably those having 1 to 3 carbon atoms. Among the polyalkylene oxides having a degree of polymerization of 2 to 6 and terminated with a hydrophobic group, preferred are polymers of ethylene oxide, propylene oxide or butylene oxide. Particularly preferred are ethylene oxide polymers. The degree of polymerization is preferably 3 to 5, particularly preferably 3 to 4. The hydrophobic groups which terminate the polyalkylene oxide are preferably lower alkyl groups such as those having 1 to 3 carbon atoms. The mode of the termination is, for example, an ether bond or ester bond. Particularly preferred is the ether bond with an alkyl group having 1 to 3 carbon atoms, and most preferred is with methyl group. Examples of the heterocyclic rings containing two or more oxygen atoms include dioxolane and dioxane. Particularly preferred are 1,3-dioxolanyl group and 1,3-dioxanyl group. The alkyl group substituted with a polyalkylene oxide group having a degree of polymerization of 2 to 6 and terminated with a hydrophobic group or substituted with a heterocyclic ring containing two or more oxygen atoms is preferably $R_3$. The halogen ion or organic acid anion represented by Q is preferably an iodide ion, chloride ion or sulfonic acid ion. Among them, the chloride ion is more preferred. Y is preferably a methine group, and p is preferably 0.

The methine compound of the present invention is usable as a spectral sensitizing dye or anticancer agent. The methine compound of the present invention can be usually synthesized by a synthesis method described in U.S. Pat. No. 2,388,963.

Examples of the compounds of the general formula (II) of the present invention will be given below, which by no means limit the invention.

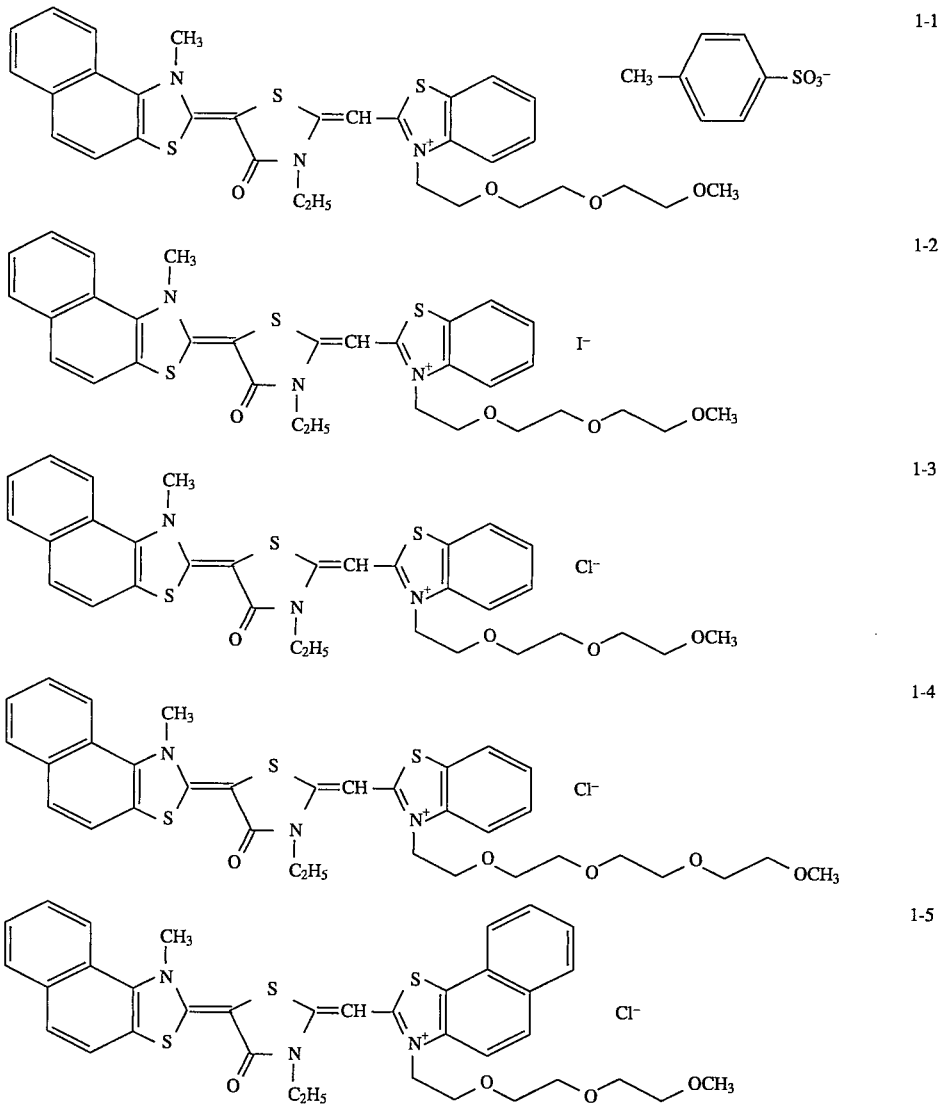

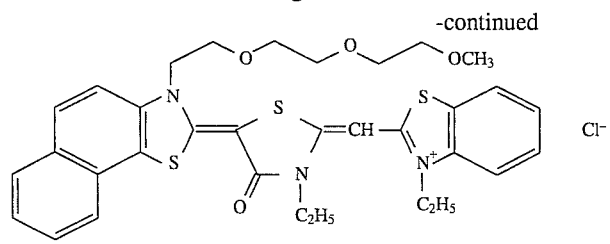
1-6
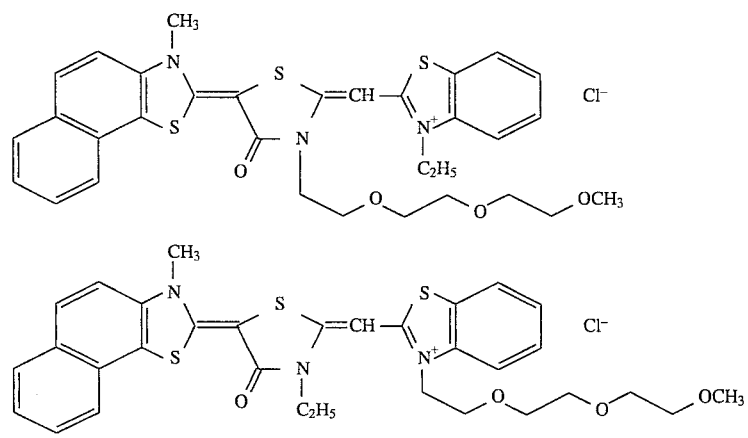
1-7
1-8
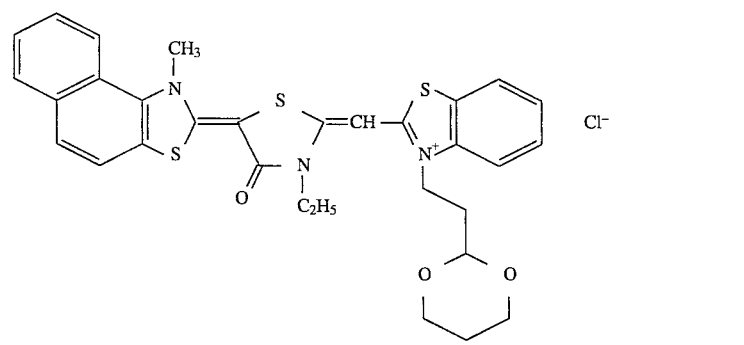
1-9
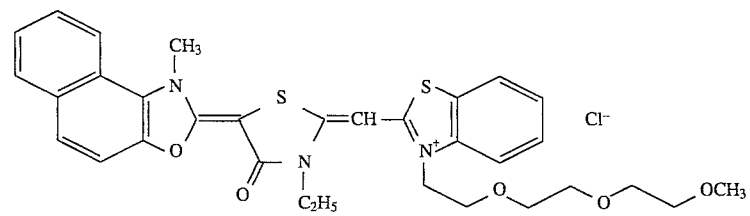
1-10
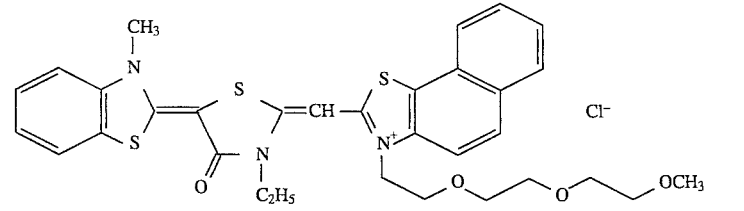
1-11
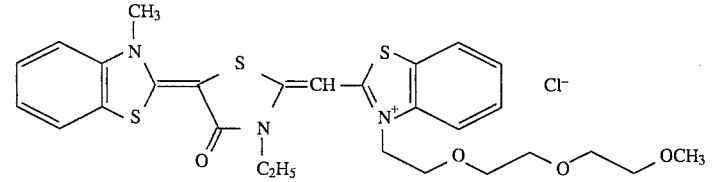
1-12

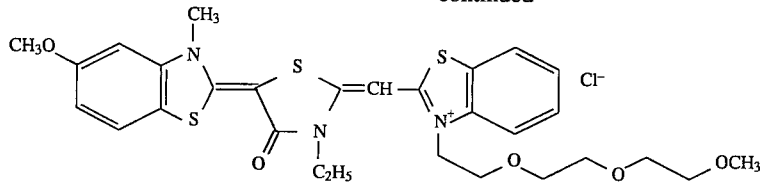

1-13

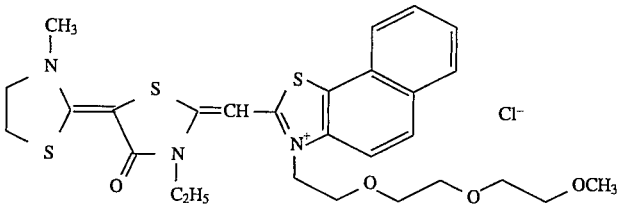

1-14

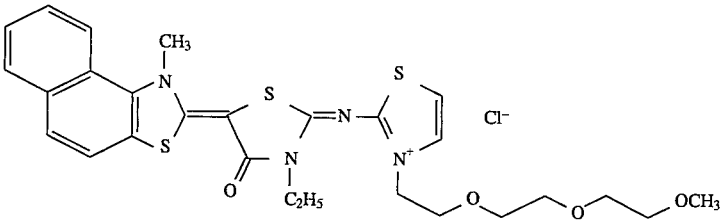

1-15

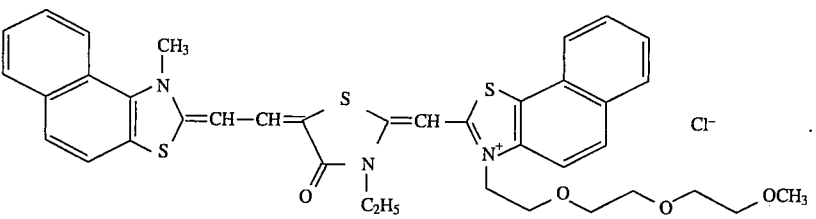

1-16

The methine compounds of the present invention are widely usable as spectral sensitizing dyes or medicines such as anticancer agents. When one of the methine compounds of the present invention is used as a medicine, it is usually administered, for example, by the following preferred method: the methine compound, dissolved in, for example, 5% glucose solution or together with a suitable carrier or diluent, is injected into a vein, abdominal cavity, muscle or bladder. In animal tests conducted for the purpose of confirming the effect of the treatment, the practical solubility suitable for the injection preparations is 0.1 to 1% by weight. By using the methine compound of the present invention, an injection preparation having a high solubility is thus provided.

Specifically, the pharmaceutical compositions of this invention containing one or more compounds of the general formulas (I) to (II) described above can be effectively used to treat various types of cancer including melanomas, hepatomas, gliomas, neuroblastomas, sarcomas and carcinomas of the lung, colon, breast, bladder, ovary, testis, prostate, cervix, pancreas, stomach, small intestine and other organs.

The pharmaceutical compositions of this invention can contain one or more compounds of the general formulas (I) to (II) and a pharmaceutically acceptable diluent and/or carrier, and if desired, can further contain other therapeutic agents including conventional anti-tumor agents known in the art. Suitable examples of such conventional anti-tumor agents which can be used include adriamycin, cisplatin, colchicine, CCNU (Lomastine), BCNU (Carmustine), Actinomycin D, 5-fluorouracil, thiotepa, cytosinearabinoside, cyclophosphamide, mitomycin C, and the like.

Suitable examples of the pharmaceutical carriers or diluents include glucose, sucrose, lactose, ethyl alcohol, glycerin, mannitol, sorbitol, pentaerythritol, diethylene glycol, triethylene glycol, ethylene glycol, propylene glycol, dipropylene glycol, polyethylene glycol 400, other polyethylene glycols, mono-, di- and triglycerides of saturated fatty acids such as glyceryl trilaurate, glyceryl monostearate, glyceryl tristearate and glyceryl distearate, pectin, starch, alginic acid, xylose, talc, lycopodium, oils and fats such as olive oil, peanut oil, castor oil, corn oil, wheat germ oil, sesame oil, cottonseed oil, sunflower seed oil and cod-liver oil, gelatin, lecithin, silica, cellulose, cellulose derivatives such as methyl hydroxypropyl cellulose, methyl cellulose, hydroxyethyl cellulose, magnesium and calcium salts of fatty acids with 12 to 22 carbon atoms such as calcium stearate, calcium laureate, magnesium oleate, calcium palmitate, calcium behenate and magnesium stearate, emulsifyers, esters of saturated and unsaturated fatty acids, e.g., having 2 to 22 carbon atoms, especially 10 to 18 carbon atoms, with monohydric aliphatic alcohols (e.g., having 1 to 20 carbon atoms such as alkanols) or polyhydric alcohols such as glycols, glycerine, diethylene glycol, pentaerythritol, ethyl alcohol, butyl alcohol, octadecyl alcohol and silicones such as dimethyl polysiloxane. Additional carriers conventionally used in pharmaceutical compositions may also be appropriate for this invention.

The pharmaceutically effective amount of the compound of the general formulas (I) to (II) and the mode or manner of administration will be dependent upon the nature of the cancer, the therapy sought, the severity of the disease, the degree of malignancy, the extent of metastatic spread, the tumor load, general health status, body weight, age, sex, and the genetic or racial background of the patient. However, in general, suitable modes of administration include intravenous, hypodermic, intraperitoneal, intramuscular or intravesicular injection or oral use in the form of, for example, a compound of the general formulas (I) to (II) in, e.g., a 5% glucose aqueous solution or with other appropriate carriers or diluents as described above. A suitable therapeutically effective amount of a compound of the general formulas (I) to (II). in the composition is about 0.01% by weight to about 10% by weight, more generally 0.1% by weight to about 1%, based on the weight of the composition.

Again, as noted above, pharmaceutically effective amounts will be generally determined by the practitioner based on the clinical symptoms observed and degree of progression of disease and like factors but a suitable therapeutically effective amount of the compound of the general formulas (I) to (II) generally can range from 10 mg to 500 mg, more generally 100 mg to 200 mg, administered per day per 70 kg of body weight, in single or multiple doses, as determined appropriate for the therapy involved.

The wide use of the methine compounds of the present invention as photosensitive materials for photography or as medicines such as anticancer agent is expected, since they have a solubility in water or the like far higher than that of an analogous rhodacyanine dye.

The following Examples will further illustrate the present invention.

EXAMPLE 1

(1) Synthesis of compound 1–1

1) Synthesis of
3-ethyl-5-(3-methylnaphtho[1,2-d]thiazolin-2-ylidene)thiazolidine-4-on-2-thion 20 g of 2-methylthio[1,2-d]naphthothiazolium=p-toluene sulfonate, 7.7 g of 3-ethylthiazoline-4-on-2-thion and 240 ml of acetonitrile were fed into a 1 l three-necked flask provided with a reflux condenser, and the resultant mixture was cooled to 0° C. 10 m l of triethylamine was added dropwise to the mixture, and the resultant mixture was stirred for 3 hours. Yellow precipitates thus formed were suction-filtered and washed with 50 ml of acetonitrile to obtain 18 g of crude crystals.

The crude crystals thus obtained and 500 ml of methanol were fed into a 1 l three-necked flask provided with a reflux condenser, and the resultant mixture was heated under reflux and stirring for 1 hour, and then cooled to 2° C. The mixture thus obtained was suction-filtered, washed with 100 ml of methanol and dried.

Yield: 97.9%.

2) Synthesis of
3-ethyl-5-(3-methylnaphtho[1,2-d]thiazolin-2-ylidene)-2-methylthio-4-oxo-2-thiazolidinium=p-toluenesulfonate 17 g of 3-ethyl-5-(3-methylnaphtho[1,2-d]thiazolin-2-ylidene)thiazolidine-4-on-2-thion and 80 ml of methyl p-toluenesulfonate were fed into a 1 E three-necked flask provided with a reflux condenser. The resultant mixture was heated to 120° C. under stirring for 4 hours. 700 ml of acetone was added to the resultant mixture. After cooling to 25° C., the precipitates thus formed were suction-filtered, washed with 100 ml of acetone and dried. M.p.: 300° C. or above.

Yield: 89%.

3) Synthesis of
3-methoxyethoxyethyl-2-methyl-benzothiazolium=p-toluenesulfonate 50 g of methoxyethoxyethyl p-toluenesulfonate, 15 ml of 2-methylbenzothiazole and 240 ml of xylene were fed into a 500 ml three-necked flask provided with a reflux condenser. The resultant mixture was heated to 110° C. under stirring for 10 hours, and then cooled to 25° C. 400 ml of ethyl acetate was added to the resultant mixture. The crystals thus formed were suction-filtered, washed with ethyl acetate and dried.

Yield: 44%.

M.p.: 70° to 7° C.

4) Synthesis of
3-methoxyethoxyethyl-2-{[3-ethyl-5-(3-methylnaphtho[1,2-d]thiazolin-2-ylidene)]-4-oxothiazolidin-2-ylidenemethyl}benzothiazolium=p-toluenesulfonate (compound 1–1)

0.5 g of 3-methoxyethoxyethyl-2-methyl-benzothiazolium=p-toluenesulfonate, 0.5 g of 3-ethyl-5-(3-methylnaphtho[1,2-d]thiazolin-2-ylidene)-2-methylthio-4-oxo-2-thiazolidinium=p-toluenesulfonate and 20 ml of acetonitrile were fed into a 100 ml three-necked flask provided with a reflux condenser. The resultant mixture was heated to 60° C. 0.26 ml of triethylamine was added dropwise to the mixture. After stirring the mixture at that temperature for 15 minutes, the reaction liquid was cooled to room temperature. 80 ml of ethyl acetate was added to the resultant mixture. The crystals thus formed were suction-filtered, washed with 50 ml of ethyl acetate and dried.

Yield: 0.54 g.

M.p.: 208° to 214° C.

(2) Synthesis of compound 1–2

1) Synthesis of
3-methoxyethoxyethyl-2-methyl-benzothiazolium=iodide 8.5 g of 2-methoxyethoxyxyl-1-iodoethane and 3.5 ml of 2-methylbenzothiazole were fed into a 300 ml three-necked flask provided with a reflux condenser. The resultant mixture was heated to 100° C. under stirring for 6 hours and then cooled to 25° C. 150 ml of ethyl acetate was added thereto. The crystals thus formed were suction-filtered, washed with ethyl acetate and dried.

Yield: 16%.

M.p.: 110° to 144° C.

2) Synthesis of
3-methoxyethoxyethyl-2-{[3-ethyl-5-(3-methylnaphtho[1,2-d]thiazolin-2-ylidene)]-4-oxothiazolidin-2-ylidenemethyl}benzothiazolium=iodide (compound 1-2)

1.25 g of 3-methoxyethoxyethoxylethyl-2-methyl-benzothiazolium=iodide, 1.25 g of 3-ethyl-5-(3-methylnaphtho[1,2-d]thiazolin-2-ylidene)-2-methylthio-4-oxo-2-thiazolidinium=p-toluenesulfonate and 125 ml of acetonitrile were fed into a 300 ml three-necked flask provided with a reflux condenser. The resultant mixture was heated to 60° C. 2 ml of triethylamine was added dropwise to the mixture. After stirring the mixture at that temperature for 15 minutes, 100 ml of ethyl acetate was added thereto, and the reaction liquid was cooled to room temperature. The crystals thus formed were suction-filtered, washed with 50 ml of ethyl acetate and dried at room temperature under reduced pressure to obtain the intended compound.

Yield: 1.2 g.

M.p.: 194° to 204° C.

(3) Synthesis of Compound 1-3

1 g of the compound 1-2, 2 ml of a strongly basic ion exchange resin (PA 318; a product of Mitsubishi Chemical Industries Ltd.) and 20 ml of methanol were fed into a 200 ml beaker. The resultant mixture was stirred at room temperature for 3 hours, passed through a column filled with the strongly basic ion exchange resin (PA 318; a product of Mitsubishi Chemical Industries Ltd.) and eluted with methanol. The eluate was collected and naturally filtered. The filtrate was concentrated under reduced pressure. The residue was dissolved in methanol, and then ethyl acetate was added to the solution to precipitate the crystals, which were then suction-filtered, washed with ethyl acetate and dried at room temperature under reduced pressure.

Yield: 1 g.

M.p.: 19° to 195° C. cl (4) Synthesis of Compound 1-4

The intended compound was obtained from 3-ethyl-5-(3-methylnaphtho[1,2-d]thiazolin-2-ylidene)-2-methylthio-4-oxo-2-thiazolidinium=p-toluenesulfonate and 3-methoxyethoxyethoxyethyl-2-methylbenzothiazolium=p-toluenesulfonate in the same manner as that of the steps of the synthesis of compound 1-3. M.p.: 170° to 180° C.

(5) Synthesis of Compound 1-5

The intended compound was obtained from 3-ethyl-5-(3-methylnaphtho[1,2-d]thiazolin-2-ylidene)-2-methylthio-4-oxo-2-thiazolidinium=p-toluenesulfonate and 3-methoxyethoxyethoxyethyl-2methylnaphtho[2,1-d]thiazolium=p-toluenesulfonate in the same manner as that of the steps of the synthesis of compound 1-3. M.p.: 160° to 170° C.

(6) Synthesis of Compound 1-6

1) Synthesis of naphtho[2,1-d]thiazoline-2-on 10.0 g of 2-methylnaphtho[2,1-d]thiazole, 15.0 g of potassium hydroxide, 0.9 g of sodium borehydride, 25 ml of ethylene glycol and 6 ml of water were fed into a 100 ml three-necked flask provided with a reflux condenser. The resultant mixture was heated at 180° C. for 12 hours, cooled to room temperature and added to 200 ml of ice/water. 15 ml of concentrated hydrochloric acid was added to the resultant mixture and the pH of the mixture was adjusted to 8 with sodium hydrogencarbonate. After extraction with 200 ml of chloroform three times followed by drying over sodium sulfate, chloroform was distilled off under reduced pressure to obtain 2-amino-1-thionaphthol. 2-Amino-1-thionaphthol thus obtained was fed into a 50 ml short-neck flask provided with a reflux condenser and heated at 180° filtered C. for 4 hours. The resultant mixture was added to 200 ml of water. After extraction with 200 ml of ethyl acetate three times followed by drying over sodium sulfate, ethyl acetate was distilled off under reduced pressure to obtain the intended compound.

Yield: 71.9%.

M.p.: 210° to 224° C.

2) Synthesis of 3-methoxyethoxyethoxyethylnaphtho[2,1-d]thiazolin-2-on 2.0 g of naphtho[2,1-d]thiazoline-2-on, 3.0 g of 2-methoxyethoxyethoxy-1-iodoethane (synthesized from methoxyethoxyethoxyethyl p-toluenesulfonate and sodium iodide), 0.6 g of potassium hydroxide and 20 ml of ethanol were fed into a 50 ml short-neck flask provided with a reflux condenser, and heated under reflux and under stirring for 4 hours. After cooling to room temperature followed by extraction with 300 ml of ethyl acetate and 150 ml of water, the thus-obtained ethyl acetate layer was dried over sodium sulfate, and ethyl acetate was distilled off under reduced pressure. The obtained compound was purified by column chromatography (hexane:ethyl acetate=1:1) to obtain the intended compound.

Yield: 51.9% (oily substance).

3) Synthesis of 3-methoxyethoxyethoxyethylnaphtho[2,1-d]thiazoline-2-thion 1.7 g of 3-methoxyethoxyethoxyethylnaphtho[2,1-d]thiazoline-2-on, 2.4 g of Lawesson's reagent and 10 ml of toluene were fed into a 50 ml short-neck flask provided with a reflux condenser. The resultant mixture was heated under reflux and stirring for 2 hours. After cooling to room temperature followed by purification by column chromatography (hexane:ethyl acetate=3:1), the intended compound was obtained.

Yield: 100% (oily substance).

4) Synthesis of 3-ethyl-5-(3-methoxyethoxyethoxyethylnaphtho[2,1-d]thiazolin-2-ylidene)thiazolidine-4-on-2-thion 1.9 g of 3-methoxyethoxyethoxyethylnaphtho[2,1-d]thiazoline-2-thion and 1.8 g of methyl p-toluenesulfonate were fed into a 50 ml short-neck flask provided with a reflux condenser. The resultant mixture was heated at 120° C. for 4 hours. After cooling the reaction mixture to room temperature followed by addition of 0.8 g of 3-ethylthiazolidine-4-on-2-thion and 24 ml of acetonitrile, the resultant mixture was cooled to 5° C., and 1.0 g of triethylamine was added thereto. After stirring at 10° C. for 24 hours, yellow precipitates thus obtained were suction-filtered, washed with 10 ml of acetonitrile three times, and dried to obtain the intended compound.

Yield: 30.0%.

5) Synthesis of 3-ethyl-2-{[3-ethyl-5-(3-methoxyethoxyethoxyethylnaphtho[2,1-d]thiazolin-2-ylidene)]-4-oxothiazolidin-2-ylidenemethyl} benzothiazolium=chloride (compound 1-6)

0.7 g of 3-ethyl-5-(3-methoxyethoxyethoxyethylnaphtho [2,1-d]thiazolin-2-ylidene)thiazolidine-4-on-2-thion), 0.8 g of methyl p-toluenesulfonate and 1 ml of dimethylformamide were fed into a 100 ml short-neck flask provided with a reflux condenser. The resultant mixture was heated at 120° C. for 3 hours. After cooling the reaction mixture to room temperature followed by addition of 0.5 g of 3-ethyl-2-methylbenzothiazolium= p-toluenesulfonate (synthesized from 2-methylbenzothiazole and ethyl p-toluenesulfonate) and 7 ml of acetonitrile, the resultant mixture was heated to 50° C. 0.6 g of triethylamine was added thereto. The resultant mixture was stirred at that temperature for 1.5 hours and then cooled to room temperature.

50 ml of ethyl acetate and 50 ml of hexane were added to the reaction mixture, and the resultant mixture was stirred at room temperature for 30 minutes. The supernatant liquid thus formed was removed. The residue was dissolved in 10 ml of methanol, and the solution was passed through a column filled with a strongly basic ion exchange resin (Diaion PA-318; a product of Mitsubishi Chemical Industries Ltd.) and eluted with methanol. The eluate was concentrated under reduced pressure. The residue was purified by column chromatography (chloroform:methanol=8:1) to obtain the intended compound.

Yield: 0.6 g.

M.p.: 254° to 257° C.

(7) Synthesis of compound 1-7

1) Synthesis of N-methoxyethoxyethoxyethylphthalimide 1.3 g of potassium phthalimide, 2-methoxyethoxyethoxy-1-iodoethane and 5 ml of dimethylformamide were fed into a 100 ml short-neck flask provided with a reflux condenser. The resultant mixture was heated at 90° c. for 3 hours. 100 ml of ethyl acetate was added thereto and the resultant mixture was cooled to room temperature. White precipitates thus obtained were suction-filtered, and the filtrate was washed with 100 ml of water. The obtained ethyl acetate layer was dried over magnesium sulfate, and ethyl acetate was distilled off under reduced pressure to obtain the intended compound.

Yield: 100% (oily substance).

2) Synthesis of 3-methoxyethoxyethoxyethylthiazolidine-4-on-2-thion 2.1 g of N-methoxyethoxyethoxyethylphthalimide, 0.4 g of hydrazine monohydrate and 3 ml of methanol were fed into a 50 ml short-neck flask provided with a reflux condenser. The resultant mixture was heated under reflux and stirring for 2 hours. The white precipitates thus formed were suction-filtered through Celite. 10 ml of triethylamine was added to the filtrate, and the resultant mixture was cooled to 5° C. 0.6 g of carbon disulfide was added to the mixture. After stirring at room temperature for 1 hour, 0.9 g of ethyl chloroacetate was added to the mixture. After stirring at 40° C. for 1 hour, the reaction mixture was added to 100 ml of water. The precipitates thus formed were suction-filtered. The obtained filtrate was subjected to the extraction with 100 ml of ethyl acetate three times and the extract was dried over magnesium sulfate. Ethyl acetate was distilled off under reduced pressure to obtain the intended compound.

Yield: 86.9% (oily substance).

3) Synthesis of 3-methoxyethoxyethoxyethyl-5-(3-methylnaphtho[2,1-d]thiazolin-2-ylidene)thiazolidine-4-on-2-thion 2.5 g of 3-methyl-2-methylthionaphtho[2,1-d]thiazolium p-toluenesulfonate (synthesized from 2-methylthionaphtho[2,1-d]thiazole and methyl p-toluenesulfonate), 1.7 g of 3-methoxyethoxyethoxyethylthiazolidine-4-on-2-thion and 30 ml of acetonitrile were fed into a 100 ml three-necked flask, and cooled to 5° C. 1.2 g of triethylamine was added to the resultant mixture. After stirring at 10° C. for 4 hours, yellow precipitates thus formed were suction-filtered, washed with 10 ml of acetonitrile twice and dried to obtain the intended compound.

Yield: 71.2%

M.p.: 188° to 192° C.

4) Synthesis of 3-methoxyethoxyethoxyethyl-5-(3-methylnaphtho[2,1-d]thiazolin-2-ylidene)-2-methylthio-4-oxo-2-thiazolium=p-toluenesulfonate 1.0 g of 3-methoxyethoxyethoxyethyl-5-(3-methylnaphtho[2,1-d]thiazolin-2-ylidene)thiazolidine-4-on-2-thion, 1.2 g of methyl p-toluenesulfonate and 2 ml of dimethylformamide were fed into a 100 ml short-neck flask provided with a reflux condenser. The resultant mixture was heated at 120° C. for 3 hours. 50 ml of ethyl acetate was added to the resultant mixture. After cooling to room temperature, yellow crystals thus formed were suction-filtered, washed with 10 ml of ethyl acetate twice and dried to obtain the intended compound.

Yield: 100%.

M.p.: 126° to 134° C.

5) Synthesis of 3-ethyl-2-{[3-methoxyethoxyethoxyethyl-5-(3-methylnaphtho[2,1-d]thiazolin-2-ylidene)]-4-oxothiazolidin-2-ylidenemethyl}benzothiazolium=chloride (compound 1-7)

1.4 g of 3-methoxyethoxyethoxyethyl-5-(3-methylnaphtho[2,1-d]thiazolin-2-ylidene)-2-methylthio-4-oxo-2-thiazolium=p-toluenesulfonate, 0.7 g of 3-ethyl-2-methylbenzothiazolinium=p-toluenesulfonate and 10 ml of acetonitrile were fed into a 100 ml three-necked flask provided with a reflux condenser, and then heated to 50° C. 0.8 g of triethylamine was added to the resultant mixture. After stirring at that temperature for 1.5 hours followed by the addition of 80 ml of ethyl acetate, the obtained mixture was cooled to room temperature. Red precipitates thus formed were suction-filtered and washed with 20 ml of ethyl acetate twice. The crystals thus obtained were dissolved in 25 ml of methanol/chloroform (4/1), and the solution was passed through a column filled with a strongly basic ion exchange resin (Diaion PA 318; a product of Mitsubishi Chemical Industries Ltd.) and eluted with methanol. The eluate was concentrated under reduced pressure. The residue was purified by column chromatography (chloroform:methanol=5:1) to obtain the intended compound.

Yield: 0.7 g.

M.p.: 228° to 235° C.

(8) Synthesis of Compound 1-8

The intended compound was obtained from 3-methoxyethoxyethoxyethyl-2-methyl-benzothiazolium=iodide and 3-ethyl-5-(3-methylnaphtho[2,1-d]thiazolin-2-ylidene)-2-methylthio-4-oxo-2-thiazolium=p-toluenesulfonate in the same manner as that of the steps of the synthesis of compound 1-3.

Yield: 0.72 g

M.p.: 228° to 235° C.

(9) Synthesis of Compound 1-9

1) Synthesis of 3-(1,3-dioxane-2-ethyl)-benzothiazolium=bromide 3.8 ml of 2-(2-bromoethyl)-1,3-dioxane and 5 ml of 2-methylbenzothiazole were fed into a 100 ml three-necked flask provided with a reflux condenser, and heated at 110° C. under stirring for 3 hours. 50 ml of acetone and 30 ml of ethyl acetate were added to the resultant mixture. After stirring at room temperature, the formed crystals were suction-filtered, washed with ethyl acetate and dried.

Yield: 8 g.

M.p.: 110° to 119° C.

2) Synthesis of 3-(1,3-dioxane-2-ethyl)-2-{[3-ethyl-5-(3-methylnaphtho[1,2-d]thiazolin-2-ylidene)]-4-oxothiazolidin-2-ylidenemethyl}benzothiazolium=chloride (compound 1-9)

0.95 g of 3-(1,3-dioxane-2-ethyl)-benzothiazolium=bromide, 1.5 g of 3-ethyl-5-(3-methylnaphtho[1,2-d]thiazolin-2-ylidene)-2-methylthio-4-oxo-2-thiazolium=p-toluenesulfonate and 30 ml of acetonitrile were fed into a 100 ml three-necked flask provided with a reflux condenser. The resultant mixture was heated to 60° C. 1 ml of triethylamine was added dropwise to the mixture. After stirring the mixture at that temperature for 5 minutes followed by addition of 100 ml of ethyl acetate, the reaction liquid was cooled to room temperature. The crystals thus formed were suction-filtered and washed with 50 ml of ethyl acetate. The crude crystals thus formed were dissolved in 50 ml of chloroform/methanol (1:1). 400 ml of ethyl acetate was added to the solution, and the crystals thus formed were suction-filtered.

The crystals thus obtained were dissolved in 100 ml of methanol/chloroform (4:1). The solution was passed through a column filled with a strongly basic ion exchange resin (PA 318; a product of Mitsubishi Chemical Industries Ltd.) and eluted with methanol. The eluate was collected and then naturally filtered. The filtrate was concentrated under reduced pressure. The residue was dissolved in methanol, and ethyl acetate was added to the solution to precipitate the crystals. The crystals were suction-filtered, washed with ethyl acetate and dried at room temperature under reduced pressure to obtain the intended compound.

Yield: 0.8 g.

M.p.: 170° to 175° C.

(10) Synthesis of Compound 1-10

The intended compound was obtained from 3-methoxyethoxyethyl-2-methyl-benzothiazolium=iodide and 3-ethyl-5-(3-methylnaphtho[2,1-d]thiazolin-2-ylidene)-2-methylthio-4-oxo-2-thiazolium=p-toluenesulfonate in the same manner as that of the steps of the synthesis of compound 1-3.

M. p.: 216° to 223° C.

(11) Synthesis of Compound 1-11

1) Synthesis of 3-methoxyethoxyethyl-2-methyl-[2,1-d]naphthothiazolium=benzenesulfonate 3.8 g of (1-methoxyethoxy)ethyl benzenesulfonate, 3 g of 2-methylnaphthothiazole and 3 ml of xylene were fed into a 200 ml three-necked flask provided with a reflux condenser, and heated at 110° C. under stirring for 5 hours. 150 ml of ethyl acetate was added to the resultant mixture. After stirring at room temperature, the formed crystals were suction-filtered, washed with ethyl acetate and dried.

Yield: 8 g.

M.p.: 80° to 88° C.

2) Synthesis of 3-ethyl-5-(3-methylbenzothiazolin-2-ylidene)-2-methylthio-4-oxo-2-thiazolium=p-toluenesulfonate 17 g of 3-ethyl-5-(3-methylbenzothiazolin-2-ylidene)thiazolidine-4-on-2-thion and 80 ml of methyl p-toluenesulfonate were fed into a 1 l three-necked flask provided with a reflux condenser, and then heated at 120° C. under stirring for 4 hours. 700 ml of acetone was added to the obtained mixture. After cooling to 25° C., the precipitates formed were suction-filtered, washed with 100 ml of acetone and dried.

M.p.: 200° to 208° C.

3) Synthesis of 3-methoxyethoxyethyl-2-{[3-ethyl-5-(3-methylbenzothiazolin-2-ylidene)]-4-oxothiazolidin-2-ylidenemethyl}naphtho[2,1-d]thiazolium=chloride (compound 1-11)

1.1 g of 3-methoxyethoxyethyl-2-methyl-[2,1-d] naphthothiazolium=benzenesulfonate, 1 g of 3-ethyl-5-(3-methylbenzothiazolin-2-ylidene)-2-methylthio-4-oxo-2-thiazolium=p-toluenesulfonate and 20 ml of acetonitrile were fed into a 200 ml three-necked flask provided with a reflux condenser. The resultant mixture was heated to 60° C. 2 ml of triethylamine was added dropwise to the mixture. After stirring the mixture at that temperature for 5 minutes followed by addition of 150 ml of ethyl acetate, the reaction liquid was cooled to room temperature. The resultant crystals were suction-filtered and then washed with 50 ml of ethyl acetate.

The crude crystals thus formed, 2 ml of a strongly basic ion exchange resin (PA 318; a product of Mitsubishi Chemical Industries Ltd.) and 150 ml of methanol/chloroform (4:1) were fed into a 300 ml beaker. After stirring at room temperature for 3 hours, the mixture was passed through a column filled with the strongly basic ion exchange resin (PA 318; a product of Mitsubishi Chemical Industries Ltd.) and eluted with methanol. The eluate was collected and then naturally filtered. The filtrate was concentrated under reduced pressure. The residue was dissolved in methanol, and ethyl acetate was added to the solution to precipitate the crystals. The crystals were suction-filtered, washed with ethyl acetate and dried at room temperature under reduced pressure to obtain the intended compound.

Yield: 0.5 g.

M.p.: 20° to 220° C.

(12) Synthesis of compound 1-12

The intended compound was obtained from 3-methoxyethoxyethyl-2-methyl-benzothiazolium=iodide and 3-ethyl-5-(3-methylbenzothiazolin-2-ylidene)-2-methylthio-4-oxo-2-thiazolium=p-toluenesulfonate in the same manner as that of the steps of the synthesis of compound 1-3.

M.p.: 236° to 23° C.

(13) Synthesis of compound 1-13

The intended compound was obtained from 3-methoxyethoxyethyl-2-methyl-benzothiazolium=iodide and 3-ethyl-5-(5-methoxy-3-methylbenzothiazolin-2-ylidene)-2-methylthio-4-oxo-2-thiazolium=p-toluenesulfonate in the same manner as that of the steps of the synthesis of compound 1-3.

M.p.: 221° to 227° C.

(14) Synthesis of compound 1-14

The intended compound was obtained from 3-ethyl-5-(3-methylthiazolin-2-ylidene)-2-methylthio-4-oxo-2-thiazolidinium=p-toluenesulfonate and 3-methoxyethoxyethoxyethyl-2-methylnaphtho[2,1-d]thiazolium=p-toluenesulfonate in the same manner as that of the steps of the synthesis of compound 1-3.

M.p.: 193° to 203° C.

(15) Synthesis of compound 1-15

1) Synthesis of 2-amino-3-methoxyethoxyethoxyethylthiazolium=p-toluenesulfonate 2-Aminothiazole and 1.4 equivalents of methoxyethoxyethoxyethyl=p-toluenesulfonate were heated on an oil bath of a temperature of 120° C. under stiring for 4 hours. Ethyl acetate was added to the resultant mixture. After the decantation, the residue was used for the subsequent reaction.

2) Synthesis of compound 1-15

The intended compound was obtained from 3-ethyl-5-(3-methylnaphtho[2,1-d]thiazoline-2-ylidene)-2-methylthio-4-oxo-2-thiazolidinium= p-toluenesulfonate and the reaction product obtained in the above step 1) in the same manner as that of the steps of the synthesis of compound 1-3.

M.p.: 85° to 92° C.

(16) Synthesis of compound 1-16

The intended compound was obtained from 3-ethyl-5-(3-methylnaphtho[1,2-d]thiazoline-2-ethylidene)-2-methylthio-4-oxo-2-thiazolidinium=p-toluenesulfonate and 3-methoxyethoxyethoxyethyl-2-methylnaptho[2,1-d]thiazolium=p-tolunesulfonate in the same manner as that of the steps of the synthesis of compound 1-3.

M.p.: 167° to 177° C.

The melting points and MNR data of the methine compounds 1-1 to 1-16 of the present invention synthesized in Example 1 are given in the following Table 1.

TABLE 1

| Compound No. | M.P. (°C.) | NMR chemical shift(DMSO-d6) TMS standard |
|---|---|---|
| 1-1 | 208–214 | σ 8.50(1H, d, 8.0Hz), 8.08(1H, d, 8.0Hz), 8.00(1H, d, 8.0Hz), 7.95(2H, dd, 8.0, 6.7Hz), 7.82(1H, d, 8.0Hz), 7.68(2H, m), 7.50(1H, dd, 20.0, 6.7Hz), 7.50(1H, d, 8.0Hz), 7.10(2H, d, 8.0Hz), 6.72(1H, s), 4.85(2H, m), 4.55(2H, m), 4.32(2H, q, 6.7Hz), 3.90(2H, m), 3.52(2H, m), 3.40(2H, m), 3.32(4H, m), 3.15(3H, s), 2.27 (3H, s), 1.30(3H, t, 6.7Hz) |
| 1-2 | 194–204 | σ 8.58(1H, d, 8.0Hz), 8.15(1H, d, 8.0Hz), 8.06(1H, d, 8.0Hz), 8.00(2H, dd, 13.0, 8.0Hz), 7.90(1H, d, 8.0Hz), 7.70(2H, dd, 8.0, 6.7Hz), 7.60(1H, d, 6.7Hz), 7.50(1H, t, 6.7Hz), 6.78 (1H, s), 4.92(2H, m), 4.55(3H, s), 4.28(2H, q, 6.7Hz), 3.90(2H, m), 3.50(2H, m), 3.40(2H, m), 3.28(4H, m), 3.15(3H, s), 1.30(3H, t, 6.7Hz) |
| 1-3 | 190–195 | σ 8.58(1H, d, 8.0Hz), 8.15(1H, d, 8.0Hz), 8.06(1H, d, 8.0Hz), 8.00(2H, dd, 13.0, 8.0Hz), 7.90(1H, d, 8.0Hz), 7.70(2H, dd, 8.0, 6.7Hz), 7.60(1H, d, 6.7Hz), 7.50(1H, t, 6.7Hz), 6.78 (1H, s), 4.92(2H, m), 4.55(3H, s), 4.28(2H, q, 6.7Hz), 3.90(2H, m), 3.50(2H, m), 3.40(2H, m), 3.28(4H, m), 3.15(3H, s), 1.30(3H, t, 6.7Hz) |
| 1-4 | 170–180 | δ 8.56(1H, d, 8.0Hz), 8.13(1H, d, 8.0Hz), 8.03(2H, t, 6.7Hz), 7.90(2H, t, 8.0Hz), 7.73 (2H, t, 6.7Hz), 7.60–7.45(2H, m), 6.73(1H, s), 4.96–4.86(2H, m), 4.56(3H, s), 4.37–4.21(2H, m), 3.98–3.87(2H, m), 3.57–3.47(2H, m), 3.47–3.34 (8H, m), 3.16(3H, s), 1.33(3H, t, 6.7Hz) |
| 1-5 | 160–170 | δ 8.53–8.37(1H, m), 8.25–7.88(4H, m), 7.83 (1H, d, 8.0Hz), 7.74–7.37(3H, m), 7.34(1H, t, 8.0Hz), 6.96(1H, t, 8.0Hz), 6.66(1H, s), 5.02–4.86 (2H, m), 4.57(3H, s), 4.34–4.14(2H, m), 4.12–3.96 (2H, m), 3.52–3.47(2H, m), 3.46–3.35(2H, m), 3.35–3.24(2H, m), 3.24–3.12(2H, m), 3.06 (3H, s), 1.32(3H, t, 6.7Hz) |
| 1-6* | 254–257 | δ 8.22(m, 1H), 7.63–7.80(m, 3H), 7.53(d, 1H, 8.0Hz), 7.21–7.45(m, 5H), 6.89(s, 1H), 4.95–5.05(m, 2H), 4.75–4.86(m, 2H), 4.64–4.75 (m, 2H), 4.10–4.20(m, 2H), 3.50–3.60 (m, 2H), 3.35–3.45(m, 2H), 3.28–3.28 (m, 2H), 3.16–3.24(m, 2H), 3.14(s, 3H), 1.35–1.47 (m, 6H) |
| 1-7* | 228–235 | δ 8.19(d, 1H, 8.0Hz), 7.82–8.06(m, 5H), 7.68(dd, 1H, 8.0, 8.0Hz), 7.51(dd, 1H, 8.0, 8.0 Hz,), 7.41(dd, 1H, 8.0, 8.0Hz), 7.33(dd, 1H, 8.0, 8.0Hz), 6.56(s, 1H), 4.50(q, 2H, 6.7Hz), 4.40(t, 2H, 6.7Hz), 4.21(s, 3H), 3.8(t, 2H, 6.7Hz), 3.57–3.61(m, 2H), 3.46–3.51(m, 2H), 3.37–3.43(m, 2H), 3.29–3.34(m, 2H), 3.08(s, 3H), 1.33(t, 3H, 6.7Hz) |

TABLE 1-continued

| Compound No. | M.P. (°C.) | NMR chemical shift(DMSO-d6) TMS standard |
|---|---|---|
| 1-8 | 228-235 | σ 8.20(1H, d, 8.0Hz), 7.94(6H, m), 7.68 (1H, t, 8.0Hz), 7.48(2H, m), 6.62(1H, s), 4.80(2H, m), 4.28(3H, s), 3.88(2H, m), 3.54 2H, m), 3.40(2H, m), 3.30(4H, m), 3.15(3H, s), 1.30(3H, t, 6.7Hz) |
| 1-9 | 170-175 | σ 8.58(1H, d, 8.0Hz), 8.16(1H, d, 8.0Hz), 8.04(2H, d, 8.0Hz), 7.90(2H, m), 7.70(2H, m), 7.55(2H, m), 6.64(1H, s), 4.74(1H, s), 4.70 2H, m), 4.55(3H, s), 4.24(2H, m), 4.00(2H, dd, 10.0, 3.3Hz), 3.68(2H, dd, 10.0, 8.0Hz), 2.10 (2H, m), 1.32(5H, m) |
| 1-10 | 216-223 | σ 8.54(1H, d, 8.0Hz), 8.26(1H, d, 8.0Hz), 8.14(1H, d, 8.0Hz), 8.00(2H, dd, 16.7, 6.7Hz), 7.92(1H, d, 8.0Hz), 7.60(4H, m), 6.80(1H, s), 4.88(2H, m), 4.55(3H, s), 4.22(2H, m), 3.90 (2H, m), 3.52(2H, m), 3.40(2H, m), 3.30(4H, m), 3.15(3H, s), 1.20(3H, t, 6.7Hz) |
| 1-11 | 208-220 | σ 8.30(1H, d, 8.0Hz), 8.17(1H, d, 8.0Hz), 8.05(1H, d, 8.0Hz), 8.05(2H, d, 6.7Hz), 7.85 (1H, d, 6.7Hz), 7.75(2H, t, 6.7Hz), 7.64(1H, d, 8.0Hz), 7.55(1H, t, 6.7Hz), 7.28(1H, t, 6.7 Hz), 7.20(1H, t, 6.7Hz), 6.75(1H, s), 5.00(2H, m), 4.22(2H, s), 4.22(3H, s), 3.94(2H, m), 3.50(2H, m), 3.45(2H, m), 3.25(2H, m), 3.15 (2H, m), 3.05(3H, s), 1.28(3H, t, 6.7Hz) |
| 1-12 | 236-238 | σ 8.20(1H, d, 8.0Hz), 7.88(1H, d, 8.0Hz), 7.75(1H, d, 9.0Hz), 7.65(1H, d, 8.0Hz), 7.48(1H, t, 8.0 Hz), 7.20(1H, d, 3.3Hz), 6.80(1H, dd, 8.0, 3.3 Hz), 6.67(1H, s), 4.80(2H, m), 4.25(2H, m), 4.18 (3H, s), 3.85(2H, m), 3.68(3H, s), 3.50(2H, m), 3.40(2H, m), 3.28(4H, m), 1.27(3H, t, 6.7Hz) |
| 1-13 | 221-227 | σ 8.20(1H, d, 8.0Hz), 7.92(2H, d, 8.0Hz), 7.75(1H, d, 8.0Hz), 7.70(1H, dd, 13.0, 8.0Hz), 7.52(1H, d, 8.0Hz), 7.42(1H, t, 8.0Hz), 7.25 (1H, t, 8.0Hz), 6.75(1H, s), 4.90(2H, m), 4.28 (2H, m), 4.20(3H, s), 3.90(2H, m), 3.50(2H, m), 3.40(2H, m), 3.28(4H, m), 3.15(3H, s), 1.27 (3H, t, 6.7Hz) |
| 1-14 | 193-203 | δ 8.40-8.06(4H, m), 7.82(1H, t, 8.0Hz), 7.72(1H, t, 8.0Hz), 6.83(1H, s), 5.07-4.96 2H, m), 4.17(2H, q, 6.7Hz), 4.05(2H, t, 8.0Hz), 3.97-3.86(2H, m), 3.53(3H, s), 3.54-3.45(2H, m), 3.26-3.17(2H, m), 3.04(3H, s), 1.23(3H, t, 6.7Hz) |
| 1-15 | 85-92 | δ 8.56(1H, d, 8.0Hz), 8.14(1H, d, 8.0Hz), 8.07(1H, d, 8.0Hz), 8.05(1H, m), 7.96(1H, d, 8.0Hz), 7.83(1H, d, 8.0Hz), 7.77-7.62(2H, m), 4.56(2H, t, 6.7Hz), 4.47(3H, s), 4.10(2H, q, 6.7Hz), 3.86(2H, t, 6.7Hz), 3.65-3.86(8H, m), 3.24(3H, s), 1.32(3H, t, 6.7Hz) |
| 1-16 | 167-177 | δ 8.17-7.25(11H, m), 6.94-6.82(2H, m), 6.54 (1H, s), 5.96(1H, d, 12Hz), 4.95-3.74(2H, m), 4.20(3H, s), 4.14-397(2H, m), 3.97-3.84(2H, m), 3.53-3.50(2H, m), 3.47-3.38(2H, m), 3.35-3.27 (2H, m), 3.26-3.17(2H, m), 3.10(3H, s), 1.26(3H, t, 6.7Hz) |

*Compound No.s 1-6 and 1-7: NMR chemical shift ($CDCl_3$)

The absorption spectrum of each of the methine compounds of the present invention synthesized in Example 1, in the form of a solution thereof in methanol, was determined. The maximum absorption wave length and molar extinction coefficient of each compound are given in Table 2.

TABLE 2

| Compound No. | $\lambda^{MeOH}_{max}$ (nm) | ε (×10$^4$) |
|---|---|---|
| 1-1 | 517 | 6.89 |
| 1-2 | 517 | 6.89 |
| 1-3 | 517 | 6.89 |
| 1-4 | 517 | 6.80 |
| 1-5 | 526 | 6.84 |
| 1-6 | 515 | 7.33 |
| 1-7 | 514 | 7.74 |
| 1-8 | 515 | 7.08 |
| 1-9 | 516 | 6.85 |
| 1-10 | 491 | 6.07 |
| 1-11 | 512 | 7.63 |

TABLE 2-continued

| Compound No. | $\lambda^{MeOH}_{max}$ (nm) | $\epsilon$ (×10⁴) |
|---|---|---|
| 1–12 | 502 | 7.41 |
| 1–13 | 510 | 7.10 |
| 1–14 | 483 | 5.38 |
| 1–15 | 462 | 4.51 |
| 1–16 | 623 | 9.74 |

EXAMPLE 2

The solubility test of each of the compounds of the present invention synthesized in Example 1 was conducted.
Conditions of experiment of solubility:

The solubility tests were conducted by the following methods of tests 1 and 2:
Test 1:

5 mg of a methine compound is fed into a test tube, to which 5 ml of ion-exchanged water is added, the resultant mixture is shaken at room temperature for 5 minutes, and the solubility thereof is macroscopically confirmed (1 mg/ml solution).
Test 2:

5mg of a methine compound is fed into a test tube, to which 0.5 ml of ion-exchanged water is added, the resultant mixture is shaken at room temperature for 5 minutes, and the solubility thereof is macroscopically confirmed (10 mg/ml solution).

The results of the solubility test 1 are given in Table 3, and those of the test 2 are given in Table 4.
Comparative compounds:

The following compounds S-1 to S-3 were used as comparative compounds:

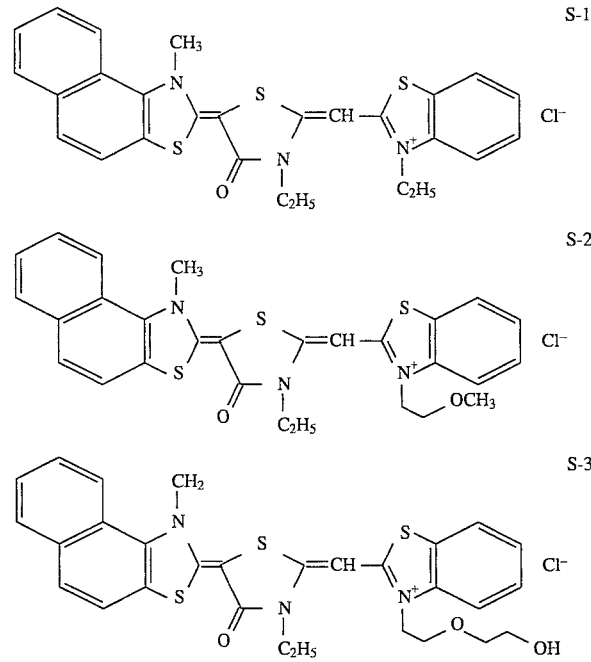

S-1

S-2

S-3

TABLE 3

| Compound No. | Solubility | |
|---|---|---|
| | 1 mg/mL | 10 mg/mL |
| 1–3 | soluble | soluble |
| 1–4 | soluble | soluble |
| 1–5 | soluble | suspension |
| 1–6 | soluble | soluble |
| 1–7 | soluble | soluble |
| 1–8 | soluble | suspension |
| 1–9 | soluble | suspension |
| 1–10 | soluble | soluble |
| 1–11 | soluble | soluble |
| 1–12 | soluble | soluble |
| 1–13 | soluble | soluble |
| 1–14 | soluble | soluble |
| 1–15 | soluble | soluble |
| 1–16 | soluble | suspension |
| S-1 | suspension | suspension |
| S-2 | suspension | suspension |
| S-3 | suspension | suspension |

In the above-described solubility tests, all of the compounds 1-3 to 1-16 of the present invention were dissolved to form a solution having a concentration of at least 1 mg/ml, while the comparative compounds S-1, S-2 and S-3 were not dissolved.

EXAMPLE 3

The solubility of each of the compounds of the present invention synthesized in Example 1 in 5% glucose solution for injection was examined.
Experimental conditions:

5 mg of a methine compound was fed into a test tube, to which 0.5 ml of 5% glucose solution for injection was added, the resultant mixture was shaken at room temperature for 5 minutes, and the solubility thereof was macroscopically confirmed (10 mg/ml solution). The results are given in Table 4.

TABLE 4

| Compound No. | Solubility 10 mg/mL |
|---|---|
| 1–3 | soluble |
| 1–4 | soluble |
| 1–7 | soluble |
| 1–8 | soluble |
| 1–10 | soluble |
| 1–11 | soluble |
| 1–12 | soluble |
| 1–13 | soluble |
| 1–14 | soluble |
| 1–15 | soluble |
| 1–16 | soluble |
| S-1 | suspension |
| S-2 | suspension |
| S-3 | suspension |

It is apparent from the results that the methine compounds of the present invention have a far higher solubility than the ordinary rhodacyanine dyes in the preparation of the injection preparations.

EXAMPLE 4

Activity of the present pharmaceutical compositions against human colonic epithelial carcinoma LS174T was determined by use of nude mouse as follows:

As the human colonic epithelial carcinoma cell lines LS174T, there was used the established line by trypsinizing piece of LS174T obtained from the operating theatre of the original adenocarcinoma of colon in such that the piece becomes suitable for cultivation. When this cultured cells LS174T are hypodermically injected to a nude mouse, the cells can be easily grown in the body of the nude mouse as a moderately to sufficiently differentiated human colonic epithelial carcinoma. The cells LS174T produce CEA in high level and can proliferate in hamster cheek pouches or immunodeprived mice, so that it has been proven that the cells LS174T have neoplastic properties.

BALB/C nu/nu mice (male, five weeks age) available from Charles River Japan Inc. were placed in an atmosphere having no pathogen. Tumors formed by the hypodermic injection of human colonic epithelial carcinoma cell lines LS174T into the mice were cut off under the aseptic condition, and the surrounding skin and connective tissue of the tumor tissues as well as the necrotic tissue located in the center of the tumor tissues were removed. The tumor tissues were Cut in the form of 3–5 mm square, and the resulting one tissue was charged into a needle for transplantation to hypodermically transplant it into the mouse. The resulting mice were randomly divided into control group (six mice) and treating group (six mice). The intravenous administration of the pharmaceutical composition into the treating group started next day. The amount and schedule of the administration were determined based on the experience, mainly the knowledge from the pretoxic-test data of LD 50 and LD 10.5% glucose solution or physiologic saline for injection was injected to the control group in the same amount as that to be intravenously injected to the treating group.

The pharmaceutical composition was dissolved in 5% glucose solution or physiologic saline for injection in such that the amount of the pharmaceutical composition contained in the glucose solution or physiologic saline is 5 ml per one kg of weight of the mouse to be injected so as to prepare an injection liquid. When the proliferation of tumor in the control group reached exponential growth phase and the size of the tumor became detectable by touch with hand, i.e., generally three weeks after the transplantation, the experiment was stopped. Then the tumor of each mouse was cut off and the weight of the resulting tumor was measured by use of chemical balance. Regarding each group, tumor inhibition percentage between the treating group and control group was calculated. The results obtained are shown in Table 5.

TABLE 5

| Compound No. | Dose (mg/kg) | Schedule (intravenous administration: day) | Tumor Inhibition Ratio (%) |
|---|---|---|---|
| 1-3 | 5 | 1 | 51.1 |
|  | 10 | 3, 7 |  |
|  | 13 | 9, 13, 15, 17 |  |
| 1-4 | 5 | 1, 3 | 71.5 |
|  | 7.5 | 6 |  |
|  | 10 | 8, 10 |  |
|  | 12.5 | 13, 15, 17 |  |
| 1-7 | 5 | 1, 17 | 83.0 |
|  | 7.5 | 3 |  |
|  | 10 | 6, 8, 10, 13 |  |
| 1-9 | 3 | 1, 4, 7 | 65.6 |
|  | 1 | 9, 11, 13, 18 |  |
| 1-11 | 8 | 1 | 67.9 |
|  | 10 | 3, 6, 8, 10, 15, 17 |  |
| 1-13 | 20 | 1, 3, 7, 11, 16, 18 | 45.2 |
|  | 25 | 9 |  |

TABLE 5-continued

| Compound No. | Dose (mg/kg) | Schedule (intravenous administration: day) | Tumor Inhibition Ratio (%) |
|---|---|---|---|
| 1-15 | 10 | 1, 3, 6, 8, 10, 13, 15 20 | 60.0 |

EXAMPLE 6

Nude Mice Bearing Human Melanoma as a Model System

LOX, a human melanoma cell line, grown subcutaneously in nude mice was excised, trypsinized to yield a single cell suspension using a metal grid with a 4 mm mesh. Red blood cells were lysed by incubation with 0.17 molar ammonium chloride at 4° C. for 20 minutes. Five million viable trypan blue negative cells made up in 0.1 ml of Dulbecco modified Eagles' medium (DME) were injected into the peritoneal cavity of a male athymic Swiss nu/nu mouse. The control group and each treatment group consisted of 5 to 10 mice. Treatment was commenced the following day by intraperitoneal injection.

Ten control mice received 0.25 ml of 2% dextrose on those days the treated groups were injected with the compounds of this invention. The compounds of the General Formulas (I) to (II) used in this invention which were tested are listed in Table 6 below and the results obtained are shown in Table 6 of the accompanying drawings. T/C is the ratio, expressed as a percentage of the mean survival age of the treated group to the mean survival age of the untreated control group.

TABLE 6

| Compounds | Dose (mg/kg) | Schedule (day) | T/C % |
|---|---|---|---|
| 1-3 | 7.5 | 1, 2, 5, 7, 9, 13, 15, 20 | 153% |
| 1-7 | 5 | 1, 9, 15 | 129% |
|  | 10 | 2, 5, 7, 13 |  |
| 1-9 | 5 | 1, 13, 15 | 153% |
|  | 10 | 2, 5, 7 |  |
|  | 15 | 9 |  |
| 1-11 | 5 | 1, 15 | 129% |
|  | 10 | 2, 5, 7, 13 |  |
|  | 15 | 9 |  |
| 1-12 | 5 | 1 | 124% |
|  | 10 | 2, 5, 7, 9, 13, 15 |  |
| 1-13 | 5 | 1 | 124% |
|  | 7.5 | 2, 5 |  |
|  | 10 | 7, 9, 13, 15 |  |

What is claimed is:

1. A methine compound represented by the following formula (I):

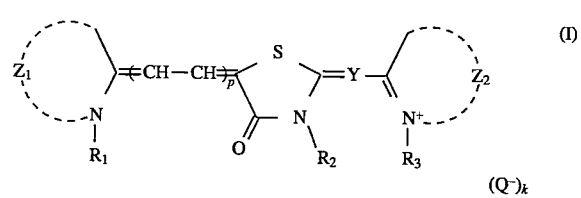

wherein $Z_1$ represents a non-metallic atomic group necessitated for forming a five-membered nitrogen-containing heterocyclic ring together with $-N(R_1)-C-$, $Z_2$ represents a non-metallic atomic group necessitated for forming a five-membered nitrogen-containing heterocyclic ring together with —N⁺(R₃)═C—, R₁, R₂ and R₃ each represent an alkyl group and at least one of R₁, R₂ and R₃ represents an alkyl group substituted with a polyethylene oxide group wherein one end of the polyalkylene oxide having a degree of polymerization of 2 to 6 is terminated with a hydrophobic group or substituted with a heterocyclic ring containing two or more oxygen atoms, Q represents an anion, k represents a numeral necessitated to control the charge in the molecule at zero, p represents 0 or 1, and Y represents a methine group or nitrogen atom.

2. The methine compound of claim 1 which is represented by the following formula (II):

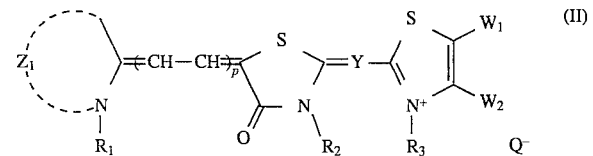

wherein $Z_1$ represents a non-metallic atomic group necessitated for forming a thiazolidine ring, a benzothiazoline ring, a benzoxazoline ring, a naphthothiazoline ring or a naphthoxazoline ring together with —N(R₁)—C—, $W_1$ and $W_2$ each represent a hydrogen atom or they together form a non-metallic atomic group necessitated for forming a naphthalene condensed ring or benzene condensed ring, Q represents a halogen ion or organic acid anion, p represents 0 or 1, Y represents a methine group or a nitrogen atom, $R_1$, $R_2$ and $R_3$ each represent an alkyl group and at least one of $R_1$, $R_2$ and $R_3$ has a substituent of the following formula III-a or III-b:

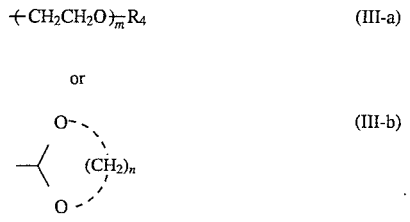

wherein $R_4$ represents an alkyl group having 2 or less carbon atoms, m represents 3 or 4 and n represents 2 or 3.

3. A methine compound of claim 2 wherein $Z_1$ together with —N(R₁)—C— forms a thiazolidine ring, a benzothiazolidine ring, a benzoxazoline ring, a naphthothiazolidine ring or a naphthoxazoline ring, each of which rings unsubstituted the number of carbon atoms of the alkyl groups $R_1$, $R_2$ and $R_3$ excluding the alkyl group substituted with the polyethylene oxide group or the heterocyclic ring is 5 or below, and Q represents an iodine ion, a chloride ion or a sulfonic acid ion.

4. The methine compound of claim 2 wherein $Z_1$ together with —N(R₁)—C— forms a thiazolidine ring, a benzothiazolidine ring, a benzoxazoline ring, a naphthothiazolidine ring or a naphthoxazoline ring, each of which rings has a substituent selected from the group consisting of a halogen atom, an alkyl group, an alkoxy group and a hydroxyl group, the number of carbon atoms of the alkyl groups $R_1$, $R_2$ and $R_3$ excluding the alkyl group substituted with the polyethylene oxide group or the heterocyclic ring is 5 or below, and Q represents an iodine ion, a chloride ion or a sulfonic acid ion.

5. The methine compound of claim 2 wherein $Z_1$ together with —N(R₁)—C— forms an unsubstituted benzothiazolidine ring or an unsubstituted naphthothiazolidine ring, the number of carbon atoms of the alkyl groups $R_1$, $R_2$ and $R_3$ excluding the alkyl group substituted with the polyethylene oxide group or the heterocyclic ring is 5 or below, and Q represents an iodine ion, a chloride ion or a sulfonic acid ion.

6. The methine compound of claim 2 wherein $Z_1$ together with —N(R₁)—C— forms a benzothiazolidine ring or a naphthothiazolidine ring each of which rings has a substituent selected from the group consisting of a halogen atom, an alkyl group, an alkoxy group and a hydroxyl group, the number of carbon atoms of the alkyl groups $R_1$, $R_2$ and $R_3$ excluding the alkyl group substituted with the polyethylene oxide group or the heterocyclic ring is 5 or below, and Q represents an iodine ion, a chloride ion or a sulfonic acid ion.

7. The methine compound of claim 2 wherein $Z_1$ together with —N(R₁)—C— forms an unsubstituted benzothiazolidine ring or an unsubstituted naphthothiazolidine ring, $W_1$ and $W_2$ together form a benzene condensed ring or a naphthalene condensed ring, the number of carbon atoms of the alkyl groups $R_1$, $R_2$ is 1 to 3, $R_3$ is represented by the formula (III-a) wherein m is 2 to 4 and $R_4$ is an alkyl group having 1 to 3 carbon atoms, Y is a methine group and Q represents an iodine ion, a chloride ion or a sulfonic acid ion.

8. The methine compound of claim 2 wherein $Z_1$ together with —N(R₁)—C— forms a benzothiazolidine ring which has an alkoxy group of 1 to 3 carbon atoms, the number of carbon atoms of each of the alkyl groups $R_1$ and $R_2$ is 1 to 3, $R_3$ is represented by the formula (III-a) wherein m is 2 to 4 and $R_4$ is an alkyl group having 1 to 3 carbon atoms, Y is a methine group and Q represents an iodine ion, a chloride ion or a sulfonic acid ion.

9. The methine compound of claim 2 wherein $Z_1$ together with —N(R₁)—C— forms a benzothiazolidine ring which has a methoxy group as a substituent, $W_1$ and $W_2$ together form a benzene condensed ring, the number of carbon atoms of each of the alkyl groups $R_1$ and $R_2$ is 1 to 3, $R_3$ is represented by the formula (III-a) wherein m is 3 to 4 and $R_4$ is an alkyl group having 1 to 3 carbon atoms, Y is a methine group and Q represents an iodine ion, a chloride ion or a sulfonic acid ion.

10. A pharmaceutical composition for treatment of cancer which comprises:

(a) a therapeutically effective amount of a methine compound represented by the following formula (I):

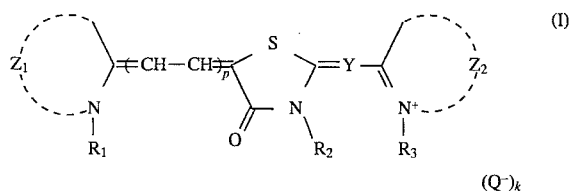

wherein $Z_1$ represents a non-metallic atomic group necessitated for forming a five-membered nitrogen-containing heterocyclic ring together with —N(R₁)—C—, $Z_2$ represents a non-metallic atomic group necessitated for forming a five-membered nitrogen-containing heterocyclic ring together with —N⁺(R₃)═C—, $R_1$, $R_2$ and $R_3$ each represent an alkyl group and at least one of $R_1$, $R_2$ and $R_3$ represents an alkyl group substituted with a polyethylene oxide group wherein one end of the polyalkylene oxide having a degree of polymerization of 2 to 6 is terminated with a hydrophobic group or substituted with a heterocyclic ring containing two or more oxygen atoms, Q represents an anion, k represents a numeral necessitated to control the charge in the molecule at zero, p represents 0 or 1, and Y represents a methine group or a nitrogen atom, and (b) a pharmaceutically acceptable diluent and/or carrier.

11. The pharmaceutical composition of claim 10 wherein the methine compound is represented by the following formula (II):

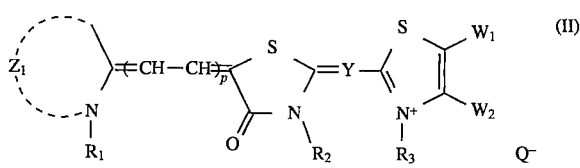

wherein $Z_1$ represents a non-metallic atomic group necessitated for forming a thiazolidine ring, a benzothiazoline ring, a benzoxazoline ring, a naphthothiazoline ring or a naphthoxazoline ring together with —N(R$_1$)—C—, $W_1$ and $W_2$ each represent a hydrogen atom or they together form a non-metallic atomic group necessitated for forming a naphthalene condensed ring or a benzene condensed ring, Q represents a halogen ion or an organic acid anion, p represents 0 or 1, Y represents a methine group or a nitrogen atom, $R_1$, $R_2$ and $R_3$ each represent an alkyl group and at least one of $R_1$, $R_2$ and $R_3$ has a substituent of the following formula III-a or III-b:

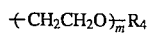 (III-a)

or

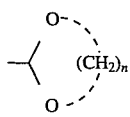 (III-b)

wherein $R_4$ represents an alkyl group having 2 or less carbon atoms, m represents 3 or 4 and n represents 2 or 3.

12. The pharmaceutical composition of claim 11 wherein $Z_1$ together with —N(R$_1$)—C— forms a thiazolidine ring, a benzothiazolidine ring, a benzoxazoline ring, a naphthothiazolidine ring or a naphthoxazoline ring, each of which rings is unsubstituted the number of carbon atoms of the alkyl groups $R_1$, $R_2$ and $R_3$ excluding the alkyl group substituted with the polyethylene oxide group or the heterocyclic ring is 5 or below, and Q represents an iodine ion, a chloride ion or a sulfonic acid ion.

13. The pharmaceutical composition of claim 11 wherein $Z_1$ together with —N(R$_1$)—C— forms a thiazolidine ring, a benzothiazolidine ring, a benzoxazoline ring, a naphthothiazolidine ring or a naphthoxazoline ring, each of which rings has a substituent selected from the group consisting of halogen atom, an alkyl group, an alkoxy group and a hydroxyl group, the number of carbon atoms of the alkyl groups $R_1$, $R_2$ and $R_3$ excluding the alkyl group substituted with the polyethylene oxide group or the heterocyclic ring is 5 or below, and Q represents an iodine ion, a chloride ion or a sulfonic acid ion.

14. The pharmaceutical composition of claim 11 wherein $Z_1$ together with —N(R$_1$)—C— forms an unsubstituted benzothiazolidine ring or an unsubstituted naphthothiazolidine ring, the number of carbon atoms of the alkyl groups $R_1$, $R_2$ and $R_3$ excluding the alkyl group substituted with the polyethylene oxide group or the heterocyclic ring is 5 or below, and Q represents an iodine ion, a chloride ion or a sulfonic acid ion.

15. The pharmaceutical composition of claim 11 wherein $Z_1$ together with —N(R$_1$)—C— forms an benzothiazolidine ring or a naphthothiazolidine ring each of which has a substituent selected from the group consisting of a halogen atom, an alkyl group, an alkoxy group and a hydroxyl group, the number of carbon atoms of the alkyl groups $R_1$, $R_2$ and $R_3$ excluding the alkyl group substituted with the polyethylene oxide group or the heterocyclic ring is 5 or below, and Q represents an iodine ion, chloride ion or a sulfonic acid ion.

16. The pharmaceutical composition of claim 11 wherein $Z_1$ together with —N(R$_1$)—C— forms an unsubstituted benzothiazolidine ring or an unsubstituted naphthothiazolidine ring, $W_1$ and $W_2$ together form a benzene condensed ring or naphthalene condensed ring, the number of carbon atoms of each of the alkyl groups $R_1$ and $R_2$ is 1 to 3, $R_3$ is represented by the formula (III-a) wherein m is 2 to 4 and $R_4$ is an alkyl group having 1 to 3 carbon atoms, Y is a methine group and Q represents an iodine ion, a chloride ion or a sulfonic acid ion.

17. The pharmaceutical composition of claim 11 wherein $Z_1$ together with —N(R$_1$)—C— forms a benzothiazolidine ring which has an alkoxy group of 1 to 3 carbon atoms, the number of carbon atoms of each of the alkyl groups $R_1$ and $R_2$ is 1 to 3, $R_3$ is represented by the formula (III-a) wherein m is 2 to 4 and $R_4$ is an alkyl group having 1 to 3 carbon atoms, Y is a methine group and Q represents an iodine ion, a chloride ion or a sulfonic acid ion.

18. The pharmaceutical composition of claim 11 wherein $Z_1$ together with —N(R$_1$)—C— forms a benzothiazolidine ring which has a methoxy group as a substitutent, $W_1$ and $W_2$ together form a benzene condensed ring, the number of carbon atoms of each of the alkyl groups $R_1$ and $R_2$ is 1 to 3, $R_3$ is represented by the formula (III-a) wherein m is 3 to 4 and $R_4$ is an alkyl group having 1 to 3 carbon atoms, Y is a methine group and Q represents an iodine ion, a chloride ion or a sulfonic acid ion.

* * * * *

UNITED STATES PATENT AND TRADEMARK OFFICE
CERTIFICATE OF CORRECTION

PATENT NO. : 5,599,825
DATED : February 4, 1997
INVENTOR(S) : Noriaki Tatsuta; Akihiko Ikegawa and Masayuki Kawakami It is certified that error appears in the above-indentified patent and that said Letters Patent is hereby corrected as shown below:

On the title page, item [75] Inventors, delete "Okegawa" and insert --Akihiko Ikegawa--.

Signed and Sealed this

Thirteenth Day of May, 1997

*Attest:*

*Attesting Officer*

BRUCE LEHMAN

*Commissioner of Patents and Trademarks*

UNITED STATES PATENT AND TRADEMARK OFFICE
CERTIFICATE OF CORRECTION

PATENT NO. : 5,599,825

DATED : February 4, 1997

INVENTOR(S) : Noriaki Tatsuta; Akihiko Ikegawa; Masayuki Kawakami; Keizo Koya;

It is certified that error appears in the above-identified patent and that said Letters Patent is hereby corrected as shown below:

On the title page, item [75], Inventors, insert as the fourth inventor --Keizo Koya--.

Signed and Sealed this

Twenty-third Day of December, 1997

Attest:

BRUCE LEHMAN

Attesting Officer

Commissioner of Patents and Trademarks